United States Patent [19]

Haines et al.

[11] Patent Number: 5,395,956
[45] Date of Patent: Mar. 7, 1995

[54] PROCESS FOR PREPARING CYCLIC ORGANOHYDROGENSILOXANES

[75] Inventors: Gregory R. Haines, Crestwood; David E. Puckett, Taylor Mill; Larry H. Wood, Campbellsburg, all of Ky.

[73] Assignee: Dow Corning Corporation, Midland, Mich.

[21] Appl. No.: 270,566

[22] Filed: Jul. 5, 1994

[51] Int. Cl.$^6$ ................................................ C07F 7/08
[52] U.S. Cl. ........................................................ 556/451
[58] Field of Search ............................................ 556/451

[56] References Cited

U.S. PATENT DOCUMENTS

| | | | |
|---|---|---|---|
| 3,590,064 | 6/1971 | Lacefield | 260/448.2 E |
| 3,714,213 | 1/1973 | Miller et al. | 260/448.2 E |
| 4,895,967 | 1/1990 | Crivello et al. | 556/451 |
| 5,189,193 | 2/1993 | Freeburne et al. | 556/451 |
| 5,241,097 | 8/1993 | Zupancic et al. | 556/451 X |

OTHER PUBLICATIONS

All–Union Electrotechnical Institute, Mar. 5, 1955, pp. 1061–1063.
Polymer, Wright et al. vol. 11, pp. 464–471 (1969).

*Primary Examiner*—Paul F. Shaver
*Attorney, Agent, or Firm*—William F. Boley

[57] ABSTRACT

A process for preparing cyclic organohydrogensiloxanes. The process comprises contacting an organohydrogendichlorosilane with about a stoichiometric equivalent of water to form a hydrolyzate. The hydrolyzate is diluted in an inert solvent and contacted with an acidic rearrangement catalyst to effect formation of cyclic organohydrogensiloxanes. The cyclic organohydrogensiloxanes are separated from inert solvent and linear organohydrogensiloxanes. The inert solvent and linear organohydrogensiloxanes are then recycled to the process for further contact with the acidic rearrangement catalyst.

20 Claims, No Drawings

PROCESS FOR PREPARING CYCLIC ORGANOHYDROGENSILOXANES

BACKGROUND OF INVENTION

The present invention is a process for preparing cyclic organohydrogensiloxanes. The process comprises contacting an organohydrogendichlorosilane with about a stoichiometric equivalent of water to form a hydrolyzate. The hydrolyzate is diluted in an inert solvent and contacted with an acidic rearrangement catalyst to effect formation of cyclic organohydrogensiloxanes.

Cyclic organohydrogensiloxanes such as cyclic methylhydrogensiloxane are useful as crosslinkers in silicone coatings and encapsulating materials used in the electronic industry and can be used as intermediates to form SiH functional siloxanes. In typical processes for preparing organohydrogensiloxanes a first step involves the hydrolysis of an organohydrogendichlorosilane to form an equilibrium mixture containing cyclic organohydrogensiloxanes and short-chain linear organohydrogensiloxanes. Generally, the weight percent of cyclic organohydrogensiloxanes in the equilibrium mixture is small in relation to the weight percent of linear organohydrogensiloxanes present. Consequently when demand for cyclic organohydrogensiloxanes is high, an excess of linear organohydrogensiloxanes may be produced. Therefore, it is an objective of the present process to provide a method to increase the proportion of cyclic organohydrogensiloxane species in the equilibrium mixture. Another objective is to provide a method where the linear species recovered from the equilibrium method can be recycled to the process for conversion to cyclic organohydrogensiloxanes. Still another objective is to provide a process where hydroxyl substitution on the silicon of the cyclic and linear species is minimized. This is necessary to prevent gelling of the linear species during conduct of the process and to provide cyclic organohydrogensiloxanes of consistent reactivity for use in other processes.

Sokolov et al., All-Union Electrotechnical Institute, Mar. 5, 1955, p. 1061-1063, teach the reaction of methydichlorosilane with water to form cyclic methylhydrogensiloxanes.

Numerous procedures have been reported in the art for improving the yield of cyclic organohydrogensiloxanes from hydrolysis processes similar to that taught by Sokolov et al.

Lacefield, U.S. Pat. No. 3,590,064, issued Jun. 19, 1971, teaches that halogen endblocked linear polysiloxanes can be reacted with at least a stoichiometric amount of an alkali metal carbonate salt in the present of a suitable polar solvent to form cyclic organopolysiloxanes. Lacefield indicates the process is suitable for forming cyclic organopolysiloxanes having hydrogen bonded to silicon.

Miller et al., U.S. Pat. No. 3,714,213, issued Jan. 30, 1973, describe a process for preparing cyclic methylhydrogensiloxanes by contacting linear methylhydrogen siloxanes with an acid catalyst absorbed on a carrier. The process requires the presence of high molecular weight chain termination groups. The yield of tetramethylcyclotetrasiloxane is reported to be about 73 percent.

Crivello et al., U.S. Pat. No. 4,895,967, issued Jan. 23, 1990, describe a method for making cyclic organohydrogensiloxanes by contacting a linear organohydrogensiloxane with a heated bed of a cracking catalyst at reduced pressure. The resulting volatile cyclic organohydrogensiloxane is then recovered. A typical yield for the method is reported to be about 85 percent.

Wright et al., Polymer, Vol. 11, p. 464–471, 1969 teach the equilibration of tetramethylcyclotetrasiloxane at 0° C. using n-butyl lithium as catalyst and about 2% tetrahydrofuran as promoter. Wright et al. report that the equilibration has to be carried out at low temperature with exclusion of moisture and oxygen in order to prevent crosslinking of the formed linear siloxanes. Wright et al. teach that if a diluent is used in the equilibration process, the weight fraction of cyclics should increase with increasing dilution up to a critical point beyond which linear polymers will be effectively absent.

The present inventors have found that when a hydrolyzate is formed by contacting an organohydrogendichlorosilane with about stoichiometric water, that this hydrolyzate can be rearranged in the presence of an acid catalyst and an inert solvent to form cyclic organohydrogensiloxanes. The process allows for linear organohydrogensiloxanes separated from the cyclic organohydrogensiloxanes to be continuously recycled to the rearrangement process, reducing the amount of linears produced by the process. Furthermore, under the conditions of the process the formation of hydroxyl substituted siloxanes is minimized as well as scission of hydrogen and organic substituents from the silicon atoms. Thus a process is provided where minimal loss of siloxanes occurs due to crosslinking of the siloxanes to high molecular weight byproducts having less utility and which may serve to plug the processing apparatus.

SUMMARY OF INVENTION

The present invention is a process for preparing cyclic organohydrogensiloxanes. The process comprises contacting an organohydrogendichlorosilane with about a stoichiometric equivalent of water to form a hydrolyzate. The hydrolyzate is diluted in an inert solvent and contacted with an acidic rearrangement catalyst to effect formation of cyclic organohydrogensiloxanes. The cyclic organohydrogensiloxanes are then separated from inert solvent and linear organohydrogensiloxanes. The inert solvent and linear organohydrogensiloxanes are then recycled to the process for further contact with the acidic rearrangement catalyst.

DESCRIPTION OF INVENTION

The present invention is a process for preparing cyclic organohydrogensiloxanes. The process comprises:

(A) contacting a silane described by formula $$RHSiCl_2 \tag{1}$$

with about a stoichiometric equivalent of water to form a hydrolyzate comprising cyclic organohydrogensiloxanes and linear organohydrogensiloxanes, (B) contacting the hydrolyzate with an acidic rearrangement catalyst in the presence of an inert solvent thereby increasing the ratio of the cyclic organohydrogensiloxanes to the linear organohydrogensiloxanes in the hydrolyzate, and (C) recovering the cyclic organohydrogensiloxanes; where R is selected from a group consisting of saturated monovalent hydrocarbon radicals comprising one to 12 carbon atoms and aryl radicals.

Silanes which can be hydrolyzed in the present process are described by formula (1). The silane may be a single species of silane as described by formula (1) or may be a mixture of such silanes. The silane contains substituent R, where R is selected from a group consisting of saturated monovalent hydrocarbon radicals comprising one to 12 carbon atoms and aryl radicals. R can be, for example, methyl, ethyl, propyl, isopropyl, butyl, tertiary butyl, sec-butyl, hexyl, cyclohexyl, dodecyl, phenyl, tolyl, and naphthyl. Preferred is when R is selected from a group consisting of methyl and phenyl. Most preferred is when R is methyl.

The silane is contacted with about a stoichiometric equivalent of water, where a stoichiometric equivalent of water is defined as 0.5 mole of water per mole of chlorine provided to the process by the silane. By use of the term "about" it is meant that the mole ratio of water to silane is within a range of plus or minus 15 percent of stoichiometric equivalence. Preferred is when the mole ratio of water to silane is within a range of minus 15 to plus 10 percent of stoichiometric equivalence. Even more preferred is when the mole ratio of water to silane is within a range of minus seven to plus five percent of stoichiometric equivalence. Most preferred is when the mole ratio of water to silane within a range of minus five percent stoichiometric equivalence to stoichiometric equivalence.

Contact of the silane with the water can be conducted in standard reactors for hydrolyzing chlorosilanes. Although the pressure at which the process is conducted is not critical, it is preferred that the process be conducted at a pressure at which the silane is present as a liquid phase. Such pressure will be dependent upon the particular chlorosilane and the temperature at which the process is conducted.

The hydrolysis process can be conducted at a temperature within a range from greater than about minus 15° C. to about 120° C. Preferred is when the hydrolysis process is conducted at a temperature within a range of about 0° C. to 50° C. Even more preferred is when the hydrolysis process is conducted at a temperature within a range of about 20° C. to 40° C.

The hydrolyzate formed in the hydrolysis process is diluted in an inert solvent. By the term "inert" it is meant a solvent which can serves as a diluent and does not otherwise have significant reaction in the process. Preferred inert solvents are those alkanes and mixtures of alkanes having a boiling point above that of the cyclic hexamer of the organohydrogensiloxane. For example when the cyclic hexamer is methylhydrogensiloxane, suitable solvents are those alkanes comprising greater than about nine carbon atoms. Inert solvents having a boiling point below that of the cyclic hexamer of the organohydrogensiloxane can also be used, but may make separation of the solvent from the cyclic organohydrogensiloxane more difficult.

The optimal weight ratio of hydrolyzate to solvent for use in the present process will depend upon such factors as the organic substituent substituted on the silicon atoms and the desired ratio of cyclic organohydrogensiloxane to linear organohydrogensiloxane in the rearranged hydrolyzate at equilibrium. Up to a certain maximum, the greater the dilution of the hydrolyzate the greater the ratio of the cyclic organohydrogensiloxanes to linear organohydrogensiloxanes in the rearranged hydrolyzate. Generally, from about 20 weight percent to 95 weight percent of solvent is useful in the present process. More preferred is about 30 weight percent to 90 weight percent solvent. Most preferred is about 60 weight percent to 85 weight percent solvent.

The diluted hydrolyzate is contacted with an acid rearrangement catalyst. Acidic rearrangement catalysts useful in the present process can be any acid which facilitates rearrangement of linear organohydrogensiloxanes to cyclic organohydrogensiloxanes. The acidic rearrangement catalyst can be a protic acid or a Lewis acid. The acidic rearrangement catalyst can be a homogeneous catalyst such as hydrogen chloride, sulfuric acid, or chlorosulfonic acid. However, such homogeneous acids are generally not preferred in the present process since they must subsequently be neutralized. Preferred is a heterogeneous catalyst which can be used in the present process, for example, as a fixed-bed or stirred-bed. The present process can be run as a continuous, semi-continuous, or batch process. Preferred is when the present process is run as a continuous process using a fixed-bed of the acidic rearrangement catalyst.

The acidic rearrangement catalyst can be, for example, a carrier such as carbon, a clay, or a zeolite having absorbed thereto a protic acid such as sulfuric or phosphoric acid. The acidic rearrangement catalyst can be, for example, an organic ion exchange resin, for example, a sulfonated divinylbenzenestyrene copolymer resin.

The temperature at which the rearrangement can be run is not critical and can generally be within a range of greater than about the freezing point of the inert solvent to about 70° C. Preferred is a temperature within a range of about 0° C. to 40° C. The pressure at which the arrangement process is run is not critical and can be ambient pressure.

Cyclic organohydrogensiloxanes are recovered from the present process. The cyclic organohydrogensiloxane which can be recovered by the present process are described by formula $(RHSiO)_n$, where R is as previously described and n is an integer from three to about 12. The preferred organohydrogensiloxanes recovered from the present process are those where R is methyl and n is four, five, or six. The method for recovering the cyclic organohydrogensiloxanes from the present process is not critical and can be standard methods known in the art for separating cyclic siloxanes from mixtures. For example, the rearranged hydrolyzate can be flash distilled to separate the cyclic organohydrogensiloxanes from higher-boiling linear organohydrogensiloxanes and the bulk of the inert high-boiling solvent. The recovered higher-boiling linear organohydrogensiloxanes and solvent can then be recycled to the rearrangement reactor. The recovered lower-boiling fraction containing the cyclic organohydrogensiloxanes can be treated with additional water to effect polymerization of low-boiling linear species to higher boiling linear species and facilitate their separation from the cyclic organohydrogensiloxanes. The resulting water phase can be removed by standard methods such as gravimetric or membrane separation. The cyclic organohydrogensiloxane containing fraction can then be distilled to separate the cyclic organohydrogensiloxanes from higher-boiling linear species. The higher-boiling linear species can then be recycled to the rearrangement reactor for further processing.

The following example is provided to illustrate the present invention. The example is not intended to limit the present claims.

EXAMPLE

Methylhydrogendichlorosilane was mixed with about a stoichiometric equivalent of water in a hydrolysis reactor i.e. 0.5 mole of water per mole of silicon bonded chlorine added to the reactor. The hydrolysis reactor was maintained at 60 psig and the temperature of the reactor was controlled such that the hydrolyzate exiting the reactor was at a temperature of about 33° C. The hydrolyzate exiting the reactor was analyzed by gas chromatography (GC) using a flame ionization detector (FID) and found to comprise about 95 weight percent linear chlorine end-terminated methylhydrogensiloxane species and about five weight percent cyclic methylhydrogensiloxanes species. The hydrolyzate was diluted to about 20 weight percent in a hydrocarbon solvent, Norpar-13, Exxon Corporation, Houston, Tex., which is a $C_{12-14}$ hydrocarbon mixture.

The diluted hydrolyzate was fed to a rearrangement reactor comprising a packed bed of sulfonated divinylbenzenestyrene copolymer, Amberlyst A-15, Rohm and Haas, Philadelphia, Pa. The rearrangement reactor was kept at ambient temperature and pressure. Residence time of the diluted hydrolyzate in the reactor was about 3-5 minutes. GC-FID analysis of the product exiting the rearrangement reactor showed the siloxane component to consist of about 70 weight percent linear chlorine end-terminated methylhydrogensiloxane species and about 30 weight percent cyclic methylhydrogensiloxane species. The product from the rearrangement reactor was vacuum flash distilled and the cyclic species and low-boiling linear species taken overhead. The bottom fraction was cooled and recycled to the rearrangement reactor.

The overhead fraction from the flash distillation was mixed with a stoichiometric equivalent of water to effect further polymerization of low molecular weight linear species. The water phase was then removed by filtration and the remaining anhydrous mixture distilled to recover the cyclic methylhydrogensiloxane species as and overhead fraction. The bottom fraction containing residual solvent and high-boiling linear methylhydrogensiloxanes was cooled and recycled to the rearrangement reactor.

The recovered cyclic methylhydrogensiloxane fraction was analyzed by GC-FID and found to comprise 99.7 weight percent cyclic methylhydrogensiloxanes of the tetramer, pentamer, and hexamer species. The process was run continuously for about 78 hours with a theoretical yield of greater than 99 percent of the chlorosilane feed being converted to cyclic methylhydrogensiloxanes.

We claim:

1. A process for preparing cyclic organohydrogensiloxanes, the process comprising:

(A) contacting a silane described by formula

with about a stoichiometric equivalent of water to form a hydrolyzate comprising cyclic organohydrogensiloxanes and linear organohydrogensiloxanes, (B) contacting the hydrolyzate with an acidic rearrangement catalyst in the presence of an inert solvent thereby increasing the ratio of the cyclic organohydrogensiloxanes to linear organohydrogensiloxanes in the hydrolyzate, and (C) recovering the cyclic organohydrogensiloxanes;

where R is selected from a group consisting of saturated monovalent hydrocarbon radicals comprising one to 12 carbon atoms and aryl radicals.

2. A process according to claim 1, where R is selected from a group consisting of methyl and phenyl.

3. A process according to claim 1, where R is methyl.

4. A process according to claim 1, where the mole ratio of water to silane is within a range of minks 15 to plus ten percent of stoichiometric equivalence.

5. A process according to claim 1, where the mole ratio of water to silane is within a range of minus five percent of stoichiometric equivalence to stoichiometric equivalence.

6. A process according to claim 1, where the silane is contacted with the water at a temperature within a range of about minus 15° C. to 120° C.

7. A process according to claim 1, where the silane is contacted with the water at a temperature within a range of about 0° C. to 50° C.

8. A process according to claim 1, where the silane is contacted with the water at a temperature within a range of about 20° C. to 40° C.

9. A process according to claim 1, where the inert solvent is selected from a group consisting of alkanes and mixtures of alkanes having a boiling point above that of cyclic organohydrogensiloxane hexamer formed by the process.

10. A process according to claim 1, where the inert solvent is about 20 weight percent to 95 weight percent of the combined weight of the inert solvent and the hydrolyzate.

11. A process according to claim 1, where the inert solvent is about 30 weight percent to 90 weight percent of the combined weight of the inert solvent and the hydrolyzate.

12. A process according to claim 1, where the inert solvent is about 60 weight percent to 85 weight percent of the combined weight of the inert solvent and the hydrolyzate.

13. A process according to claim 1, where the acidic rearrangement catalyst is a heterogeneous catalyst.

14. A process according to claim 13, where the acidic rearrangement catalyst is selected from a group consisting of carbon, clay, and zeolite having absorbed thereto a protic acid.

15. A process according to claim 14, where the acid is selected from a group consisting of sulfuric acid and phosphoric acid.

16. A process according to claim 13, where the acidic rearrangement catalyst is a sulfonated divinylbenzenestyrene copolymer resin.

17. A process according to claim 1, where the hydrolyzate is contacted with the acidic rearrangement catalyst at a temperature within a range of greater than about the freezing point of the inert solvent to about 70° C.

18. A process according to claim 1, where the hydrolyzate is contacted with the acidic rearrangement catalyst at a temperature within a range of about 0° C. to 40° C.

19. A process according to claim 1, where the process is run as a continuous process using a heterogeneous acidic rearrangement catalyst and recovered linear organohydrogensiloxanes and inert solvent is recycled to the process.

20. A process for preparing cyclic methylhydrogensiloxanes, the process comprising:

(A) contacting methylhydrogendichlorosilane with water at a temperature within a range of about 0° C. to 50° C., where the water is present within a range of minus seven to plus five percent of stoichiometric equivalence, to form a hydrolyzate comprising cyclic methylhydrogensiloxanes and linear methylhydrogensiloxanes, (B) contacting the hydrolyzate with a heterogeneous rearrangement catalyst at a temperature within a range of about 0° C. to 40° C. in the presence of 30 weight percent to 90 weight percent of an inert solvent selected from a group consisting of alkanes and mixtures of alkanes having a boiling point above that of hexamethylcyclohexasiloxane, thereby increasing the ratio of the cyclic methylhydrogensiloxanes to linear methylhydrogensiloxanes in the hydrolyzate, (C) recovering the cyclic methylhydrogensiloxanes by separation from the linear methylhydrogensiloxanes and solvent, and (D) recycling the linear methylhydrogensiloxanes and solvent from Step (C) to Step (B).

* * * * *